United States Patent
Hu et al.

(10) Patent No.: US 10,978,208 B2
(45) Date of Patent: Apr. 13, 2021

(54) PATIENT RISK STRATIFICATION BY COMBINING KNOWLEDGE-DRIVEN AND DATA-DRIVEN INSIGHTS

(71) Applicant: INTERNATIONAL BUSINESS MACHINES CORPORATION, Armonk, NY (US)

(72) Inventors: Jianying Hu, Bronx, NY (US); Buyue Qian, Ossining, NY (US); Fei Wang, Ossining, NY (US); Jun Wang, White Plains, NY (US); Xiang Wang, White Plains, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 538 days.

(21) Appl. No.: 14/097,995

(22) Filed: Dec. 5, 2013

(65) Prior Publication Data
US 2015/0161346 A1    Jun. 11, 2015

(51) Int. Cl.
G16H 50/30    (2018.01)

(52) U.S. Cl.
CPC .................................. *G16H 50/30* (2018.01)

(58) Field of Classification Search
CPC . G06F 19/345; G06F 19/3431; G06F 19/3433
USPC ........................................................ 705/2–4
See application file for complete search history.

(56) References Cited

U.S. PATENT DOCUMENTS

| | | | |
|---|---|---|---|
| 5,642,936 A | 7/1997 | Evans | |
| 5,976,082 A * | 11/1999 | Wong | G06F 19/3443 600/300 |
| 7,584,166 B2 | 9/2009 | Grichnik | |
| 7,664,662 B1 * | 2/2010 | Binns | G06Q 10/00 600/300 |
| 8,108,381 B2 * | 1/2012 | Eberholst | G06F 17/3069 707/713 |
| 8,244,654 B1 * | 8/2012 | Hobgood | G06F 19/328 600/300 |
| 8,335,698 B2 * | 12/2012 | Angell | G06Q 10/10 705/2 |
| 8,355,925 B2 | 1/2013 | Rothman et al. | |
| 2008/0082356 A1 * | 4/2008 | Friedlander | G06Q 30/02 705/2 |

(Continued)

FOREIGN PATENT DOCUMENTS

| | | |
|---|---|---|
| CN | 103336900 | 10/2013 |
| CN | 104661588 | 5/2015 |
| EP | 1262901 | 12/2002 |

OTHER PUBLICATIONS

Haq, Ihtshannul U., et al. "Is the Framingham risk function valid for northern European populations? A comparison of methods for estimating absolute coronary risk in high risk men." Heart 81.1 (1999): 40-46.*

(Continued)

*Primary Examiner* — Mark Holcomb
(74) *Attorney, Agent, or Firm* — Tutunjian & Bitetto, P.C.; Kristofer Haggerty (57) ABSTRACT

A system and method for patient stratification include determining a first set of patient groups from patients in a patient similarity graph based on a similarity structure of the patient similarity graph. A second set of patient groups is identified based on expert domain knowledge associated with the patients. Patients in the first set and the second set are aligned using a processor to stratify patients.

20 Claims, 5 Drawing Sheets

(56) References Cited

U.S. PATENT DOCUMENTS

| | | | | |
|---|---|---|---|---|
| 2009/0006130 A1* | 1/2009 | Taylor | ................... | G06Q 50/22 705/2 |
| 2010/0312798 A1* | 12/2010 | Dutta | ................... | G16H 50/70 707/780 |
| 2012/0041779 A1* | 2/2012 | Boroczky | ............. | G16H 30/20 705/2 |
| 2013/0226616 A1* | 8/2013 | Nigam | ................... | G06Q 10/00 705/3 |
| 2014/0095184 A1* | 4/2014 | Gotz | ................. | G06Q 10/0635 705/2 |
| 2014/0095186 A1* | 4/2014 | Gotz | ................. | G06Q 10/0635 705/2 |

OTHER PUBLICATIONS

Gotz, D., et al. "Identifying Group and Individual-Level Risk Factors Via Risk-Driven Patient Stratification" U.S. Appl. No. 13/632,659, filed Oct. 1, 2012. (29 Pages).

Ding, C., et al. "Nonnegative Matrix Factorization for Combinatorial Optimization: Spectral Clustering, Graph Matching, and Clique Finding" Eighth IEEE International Conference on Data Mining. Dec. 2008. pp. 183-192.

Kamvar, S., et al. "Spectral Learning" Proceedings of the Eighteenth International Joint Conference on Artificial Intelligence. Aug. 2003. pp. 561-566.

Lampert, C., et al. "Learning to Detect Unseen Object Classes by Between-Class Attribute Transfer" 2009 IEEE Computer Society Conference on Computer Vision and Pattern Recognition. Jun. 2009. (8 Pages).

Liu, B., et al. "Partially Supervised Classification of Text Documents" ICML Proceedings of the Nineteenth International Conference on Machine Learning. 2002. (13 Pages).

Nie, F., et al. "A General Graph-Based Semi-Supervised Learning With Novel Class Discovery" Neural Computing and Applications. vol. 19, No. 4. Jun. 2010. (8 Pages).

Palatucci, M., et al. "Zero-Shot Learning With Semantic Output Codes" 23rd Annual Conference on Neural Information Processing Systems. Dec. 2009. pp. 1-9.

Wang, F., et al. "Label Propagation Through Linear Neighborhoods" Proceedings of the 23rd International Conference on Machine Learning. IEEE Transactions on Knowledge and Data Engineering. vol. 20, No. 1. Jan. 2008. (8 Pages).

Wu, J., et al. "Prediction Modeling Using EHR Data Challenges, Strategies, and a Comparison of Machine Learning Approaches" Medical Care. vol. 48, No. 6. Jun. 2010. pp. 106-113.

Yang, T., et al. "Unsupervised Transfer Classification: Application to Text Categorization" Proceedings of the 16th ACM SIGKDD International Conference on Knowledge Discovery and Data Mining. Jul. 2010. (10 Pages.).

Zhang, D., et al. "Serendipitous Learning: Learning Beyond the Predefined Label Space" Proceedings of the 17th ACM SIGKDD International Conference on Knowledge Discovery and Data Mining. Aug. 2011. pp. 1343-1351.

Zhou, D., et al. "Learning With Local and Global Consistency" Advances in Neural Information Processing Systems. NIPS 2003. Dec. 2003. (8 Pages).

* cited by examiner

Formulating an objective function
702

Determining a first set of patient groups from patients in a patient similarity graph based on a similarity structure of the patient similarity graph
704

The patient similarity graph includes nodes representing patients and edges representing similarity between patients
706

Identifying a second set of patient groups based on expert domain knowledge associated with the patients
708

The expert domain knowledge includes known risk groups with associated risk factors and / or known risk factors
710

Aligning patients in the first set and the second set to stratify patients
712

Identifying additional patients groups that are not associated with the expert domain knowledge
714

Maximizing an agreement between patients assigned to the first set and patients assigned to the second set
716

Iteratively minimizing the objective function until convergence
718

FIG. 7

PATIENT RISK STRATIFICATION BY COMBINING KNOWLEDGE-DRIVEN AND DATA-DRIVEN INSIGHTS

BACKGROUND

Technical Field

The present invention relates to risk group identification, and more particularly to combining knowledge-driven insights and data-driven insights for risk group identification from a patient similarity network.

Description of the Related Art

Personalized care is one of the major trends in modern medical informatics, where a key step is to segment the patient cohort into homogeneous groups so that a customized treatment plan can be constructed for each group. Patient risk stratification can be viewed as a specific way of patient cohort segmentation such that patients in each group share similar risks of having an adverse outcome, e.g., the onset of congestive heart failure (CHF).

A major challenge for risk stratification is the heterogeneity of patients' clinical conditions. For instance, CHF patients have different comorbidities, such as diabetes, kidney diseases, lung diseases, etc. In different comorbidity groups, the medical features that contribute to the risk, or risk factors, are different. Even for the common risk factors across different patient groups, their contributions to the risk score could vary significantly. For example, asthma is a known risk factor for heart disease, but it will contribute much more to the heart disease risk for patients with other existing lung diseases than patients with diabetes. Therefore, constructing a universal risk prediction model using a shared set of risk factors may not be the best approach for risk stratification. It makes more sense to first segment the patient cohort into risk groups with consistent clinical conditions, and then construct the prediction model using customized risk factors from each group.

In order to accurately segment the patient cohort, prior knowledge should be incorporated from domain experts (e.g., physicians). On the one hand, it is very important to incorporate this domain knowledge (often in the form of known risk factors) because they reflect crucial medical insights that are validated by extensive clinical studies. On the other hand, this domain knowledge is mostly incomplete because the domain experts can only provide guidance within their areas of expertise, which are unlikely to cover all the relevant medical aspects of any given patient cohort.

SUMMARY

A method for patient stratification includes determining a first set of patient groups from patients in a patient similarity graph based on a similarity structure of the patient similarity graph. A second set of patient groups is identified based on expert domain knowledge associated with the patients. Patients in the first set and the second set are aligned using a processor to stratify patients.

A system for patient stratification includes a data driven identification module configured to determine a first set of patient groups from patients in a patient similarity graph based on a similarity structure of the patient similarity graph. A knowledge driven identification module is configured to identify a second set of patient groups based on expert domain knowledge associated with the patients. A matching module is configured to align patients in the first set and the second set using a processor to stratify patients.

These and other features and advantages will become apparent from the following detailed description of illustrative embodiments thereof, which is to be read in connection with the accompanying drawings.

BRIEF DESCRIPTION OF DRAWINGS

The disclosure will provide details in the following description of preferred embodiments with reference to the following figures wherein.

DETAILED DESCRIPTION OF PREFERRED EMBODIMENTS

In accordance with the present principles, systems and methods for patient risk stratification are provided by combining knowledge-driven and data-driven insights. The present principles formulate an objective function that receives as input a patient similarity graph and expert knowledge domain (e.g., known risk factors) and outputs a set of patient risk groups that align with the known risk factors. The objective function is formulated to determine a first set of patient risk groups from patients in a patient similarity graph based on a similarity structure of the patient similarity graph. A second set of patient risk groups are identified based on expert domain knowledge associated with the patients. Patients in the first set and second set are aligned for patient stratification. The present principles may discover data-driven risk groups that are not covered by the knowledge-driven risk factors. An efficient solution is proposed based on Block Coordinate Descent to solve the objective function.

Advantageously, the present principles are graph-based and, therefore, can identify risk groups from a patient similarity network without access to the raw clinical features. Also, the present principles can incorporate incomplete and very sparse domain knowledge.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electro-magnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing. Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The flowchart and block diagrams in the Figures illustrate the architecture, functionality, and operation of possible implementations of systems, methods and computer program products according to various embodiments of the present invention. In this regard, each block in the flowchart or block diagrams may represent a module, segment, or portion of code, which comprises one or more executable instructions for implementing the specified logical function(s). It should also be noted that, in some alternative implementations, the functions noted in the blocks may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts, or combinations of special purpose hardware and computer instructions.

Reference in the specification to "one embodiment" or "an embodiment" of the present principles, as well as other variations thereof, means that a particular feature, structure, characteristic, and so forth described in connection with the embodiment is included in at least one embodiment of the present principles. Thus, the appearances of the phrase "in one embodiment" or "in an embodiment", as well any other variations, appearing in various places throughout the specification are not necessarily all referring to the same embodiment.

It is to be appreciated that the use of any of the following "/", "and/or", and "at least one of", for example, in the cases of "A/B", "A and/or B" and "at least one of A and B", is intended to encompass the selection of the first listed option (A) only, or the selection of the second listed option (B) only, or the selection of both options (A and B). As a further example, in the cases of "A, B, and/or C" and "at least one of A, B, and C", such phrasing is intended to encompass the selection of the first listed option (A) only, or the selection of the second listed option (B) only, or the selection of the third listed option (C) only, or the selection of the first and the second listed options (A and B) only, or the selection of the first and third listed options (A and C) only, or the selection of the second and third listed options (B and C) only, or the selection of all three options (A and B and C). This may be extended, as readily apparent by one of ordinary skill in this and related arts, for as many items listed.

Figure 1:
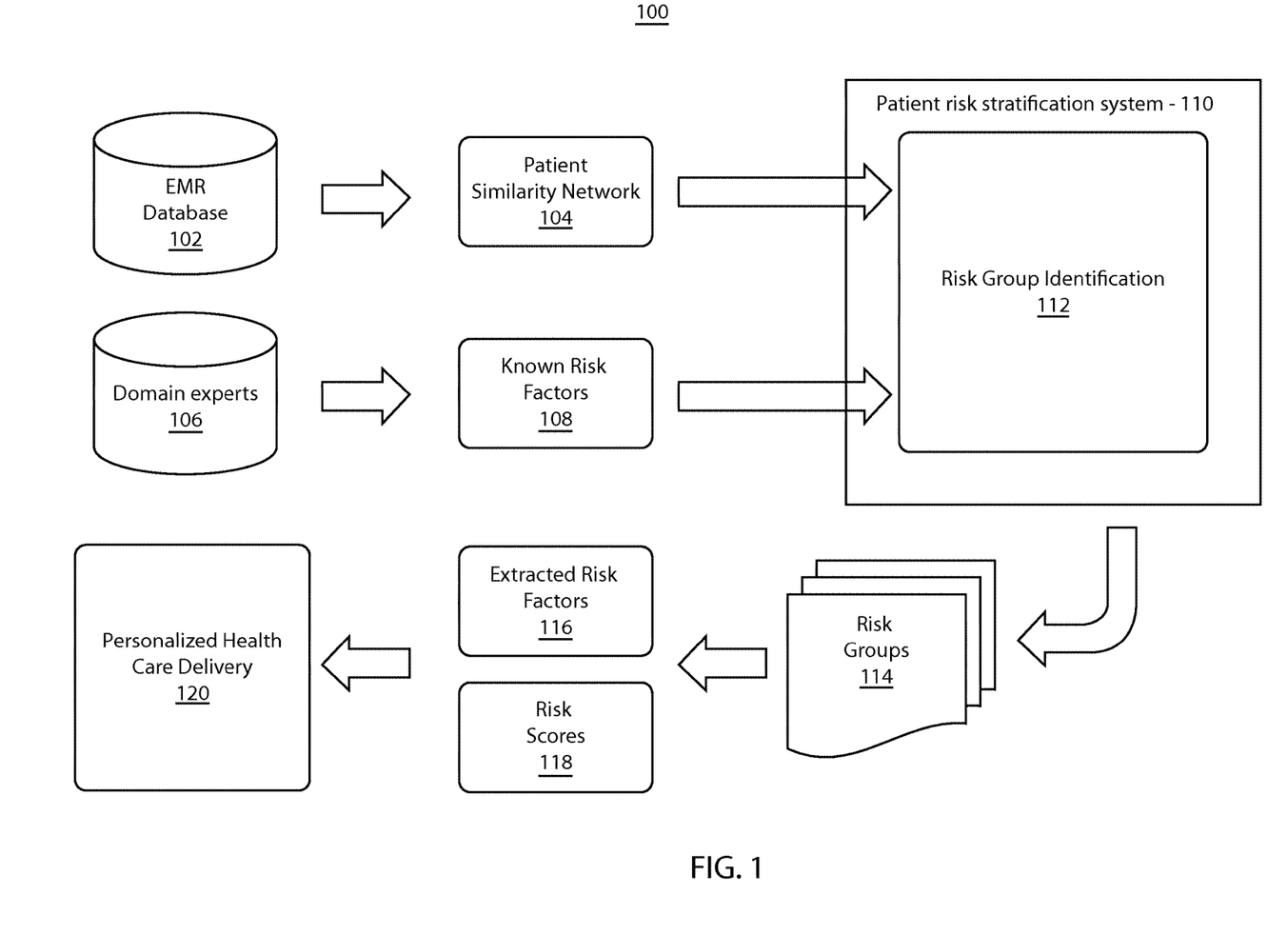
FIG. 1 is high-level block/flow diagram showing a patient risk stratification system in accordance with one illustrative embodiment.

Referring now to the drawings in which like numerals represent the same or similar elements and initially to FIG. 1, a block/flow diagram showing a high-level overview of a patient risk stratification system 100 is illustratively depicted in accordance with one embodiment. The patient risk stratification system 100 includes a novel semi-supervised learning framework for data- and knowledge-driven patient risk group exploration.

Electronic medical records (EMR) database 102 includes medical event data for a cohort of patients. The cohort of patients may be selected based on a condition of interest (e.g., disease, anatomy, etc.). EMR database 102 is employed to generate a patient similarity network 104. The patient similarity network 104 includes a graph having nodes as patients and edges as patient similarities. Domain experts 106 may include physicians or other experts. Domain experts 106 preferably provide a set of known risk factors 108.

The patient risk stratification system 110 receives the patient similarity network 104 and known risk factors 108 as inputs. Risk group identification 112 is performed, which results in a set of patient risk groups 114 that align with those provided risk factors 108. Risk factors 116 are extracted from the risk groups 114 and risk scores 118 are estimated for each risk factor. The risk factors 116 and associated risk scores 118 may be used, e.g., for patient similarity learning, guided risk stratification, clinical pathway study, visualization, etc. in a personalized health care delivery system 120.

It should be understood that while the present invention will be discussed with regards to patients and medical conditions for application in the medical field, the present invention is not so limited. For example, the present invention may be applicable determine groups from any data having incomplete knowledge. Other applications are also contemplated within the context of the present principles.

Figure 2:
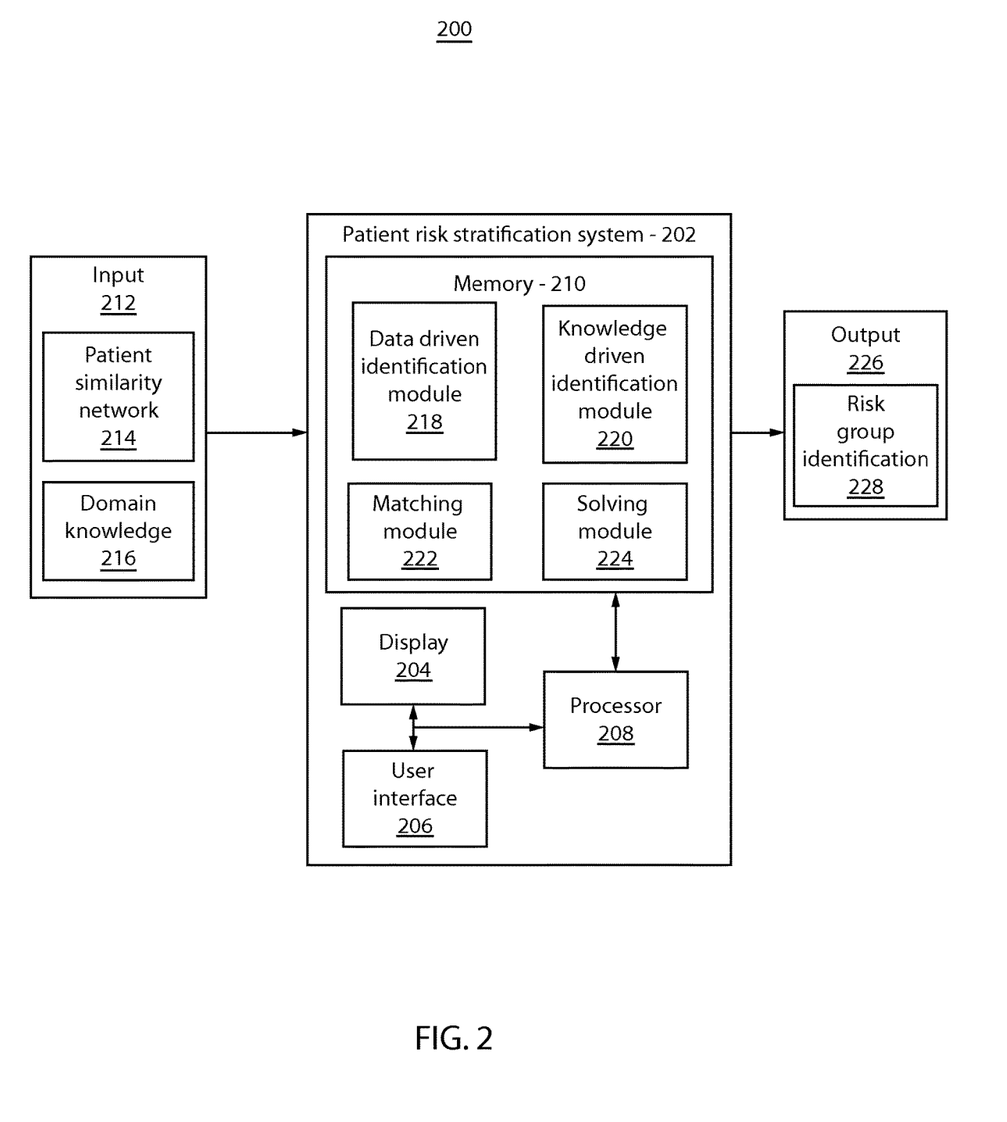
FIG. 2 is a block/flow diagram showing a system for patient risk stratification in accordance with one illustrative embodiment.

Referring now to FIG. 2, a block/flow diagram showing a system 200 for patient risk stratification is illustratively depicted in accordance with one embodiment. The patient risk stratification system 200 permits the incorporation of expert domain knowledge into the risk group discovery process to ensure that identified groups are clinically meaningful and coherent.

The system 200 may include a patient risk stratification system or workstation 202. The system 202 preferably includes one or more processors 208 and memory 210 for storing applications, modules and other data. The system 202 may also include one or more displays 204 for viewing. The displays 204 may permit a user to interact with the system 202 and its components and functions. This may be further facilitated by a user interface 206, which may include a mouse, joystick, or any other peripheral or control to permit user interaction with the system 202 and/or its devices. It should be understood that the components and functions of the system 202 may be represented as one or more discrete systems or workstations, or may be integrated as part of a larger system or workstation, such as, e.g., a personalized health care delivery system.

The system 202 may receive input 212, which may include patient similarity network 214 and domain knowledge 216. The patient similarity network 214 may include a graph where nodes represent patients and edges represent similarities between the patients (e.g., similar medical conditions). The patient similarity network 214 is preferably formed from data-driven insights, e.g., patient data from an EMR database. The domain knowledge 216 preferably includes known risk factors from experts (e.g., physicians) about one or more (but preferably not all) patients. However, domain knowledge 216 may also include other information, such as, e.g., treatment received by certain patients (drugs, procedures, etc.), clinical pathway (temporal analysis), or other information from alternative sources.

Figure 3:
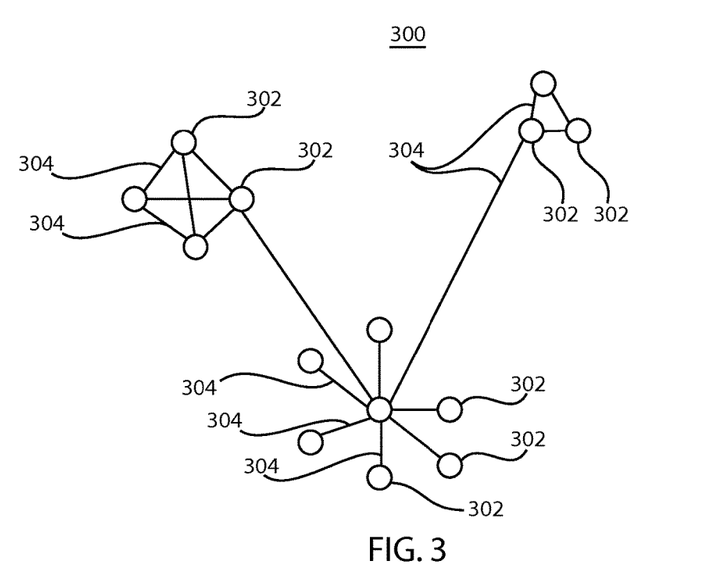
FIG. 3 shows an exemplary patient similarity network graph in accordance with one illustrative embodiment.

Referring for a moment to FIG. 3, an exemplary patient similarity network graph 300 is illustratively depicted in accordance with one embodiment. The patient similarity network graph includes exemplary nodes 302 and edges 304. The nodes 302 represent patients. The edges 304 represent a similarity between two nodes 302, such as, e.g., a similar medical condition.

Assume a cohort of n patients with their similarity matrix $W \in R^{n \times n}$, whose (i, j)-th entry encodes the clinical similarity between patient i and patient j. W is symmetric. Let $\Delta$ be the corresponding normalized graph Laplacian. Suppose there are c knowledge-driven risk factors 216, and $Y=[y_1, \ldots, y_c] \in \{0,1\}^{n \times c}$ encodes their association to the patients, i.e., $y_{ij}=1$ means patient i has risk factor j (so that patient i belongs to risk group j; note that such group assignment can be overlapping, i.e., one patient can belong to multiple groups based on the risk factors he/she has), $y_{ij}=0$ otherwise. Let $L \subset \{1, \ldots, n\}$ denote the index set of labeled patients and c' be the total number of risk groups. Assume c'>c, i.e., some risk groups are unseen with unknown risk factors. Let $F=[f_1, \ldots f_c] \in \{0,1\}^{n \times c}$ be the patient assignment matrix to the knowledge-driven risk groups, and $G=[g_1, \ldots g_{c'}] \in \{0,1\}^{n \times c'}$ be the patient assignment matrix to all potential risk groups.

The following objective is formulated in equation 1.

$$\mathcal{J} = \alpha \sum_{k=1}^{c} \|f_k - y_k\|_L^2 + \beta \sum_{K=1}^{c} f_k^T \Delta f_k + \gamma \sum_{l=1}^{c'} g_l^T \Delta g_l - \mu \sum_{k=1}^{c} \sum_{l=1}^{c'} g_l^T (f_k f_k^T) g_l \quad (1)$$

where $\alpha, \beta, \gamma, \mu > 0$ are all weighting parameters. The goal is to minimize J. The meaning of each term in J will be discussed in the following section.

The data driven identification module 218 is configured to identify risk groups using only data-driven insights (i.e., the patient similarity network 214) based on unsupervised learning. Data driven insights are extracted from an EMR database or other sources of medical data to build the patient similarity network graph 300 such that patients in the same risk group are similar to each other according to their clinical conditions. Risk groups may be labeled by conditions of interest (e.g., disease, anatomy, etc.). Patients of a risk group may be associated with risk factors, such as, e.g., diabetes, heart arrhythmias, glaucoma, etc. However, risk groups identified with only data-driven insights may be incomplete, e.g., having unseen classes (i.e., unknown risk groups), missing risk factors, etc.

The data driven identification module 218 formulates the group term in equation 1:

$$\gamma \sum_{l=1}^{c'} g_l^T \Delta g_l.$$

Note that G is the assignment of patients to all c' potential risk groups. This grouping term represents the data-driven exploration of the graph structure Δ. γ decides how much G will be biased towards the normalized min-cut of the graph.

Figure 4:
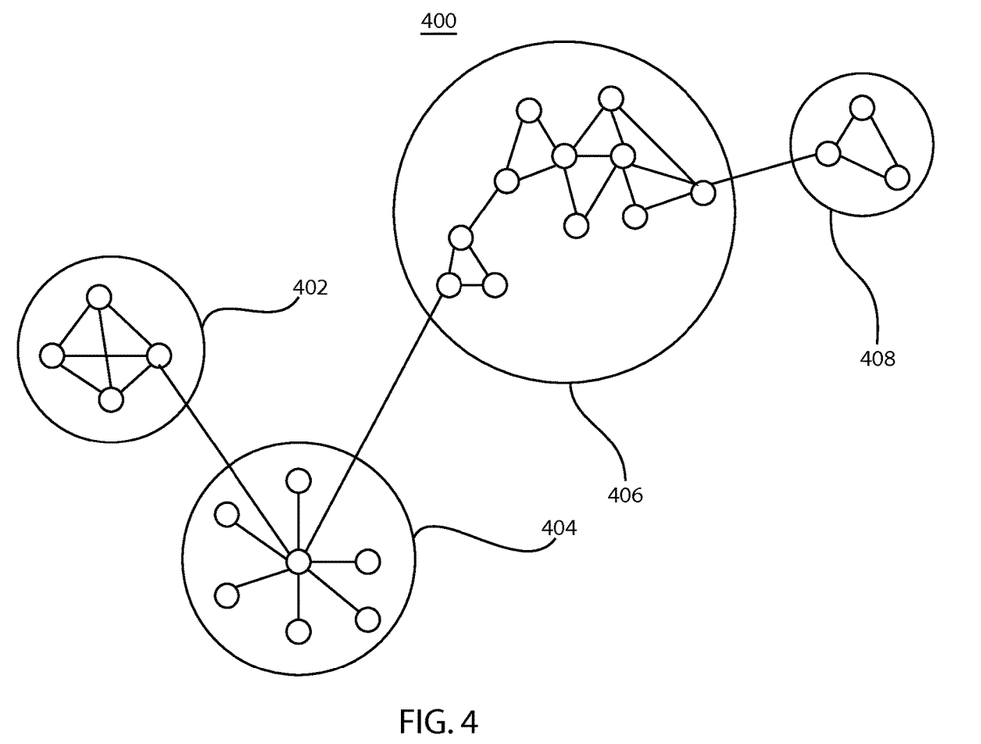
FIG. 4 shows an exemplary patient similarity network graph having risk groups identified from data-driven insights only in accordance with one illustrative embodiment.

Referring for a moment to FIG. 4, an exemplary patient similarity network graph 400 is illustratively depicted in accordance with one embodiment. The patient similarity network graph 400 is shown having risk groups 402, 404, 406, 408 identified using data-driven insights only. The risk groups are classes being labeled in patient similarity network graph 400 by medical condition. For example, risk group 402 may be labeled "skin disease" having risk factors such as dermatoses, malignant neoplasm of skin, etc., risk group 404 may be labeled "heart disease" having risk factors such as heart arrhythmias, chronic ischemic heart disease, etc., risk group 406 may have an unknown label with risk factors such as diabetes, chronic renal failure, etc., and risk group 408 may be labeled "eye disease" having risk factors such as glaucoma, cataract, etc. As can be seen from risk group 406, risk groups identified with only data-driven insights may be incomplete (e.g., unseen classes, missing risk factors, etc.).

Referring back to FIG. 1, knowledge driven identification module 220 is configured to identify risk groups using domain experts 216, preferably in the form of known risk factors, using semi-supervised learning. The data driven identification module 218 and the knowledge driven identification module 220 may use either the same patient similarity network or different patient similarity networks. This allows the combination of knowledge-driven insights derived from one domain and data-driven insights derived from another domain. The knowledge driven identification module 220 formulates the fitting term and smoothing term in equation 1.

The knowledge driven identification module 220 formulates the fitting term in equation 1:

$$\alpha \sum_{k=1}^{c} \|f_k - y_k\|_{\mathcal{L}}^2.$$

Note that F is the assignment of patients to the c knowledge-driven risk groups. This term governs how well F must fit the input knowledge Y. The subscript L means the fitting only applies to labeled patients. α decides how much F can deviate from Y. When α→∞, the known labels are not allowed to be altered.

The knowledge driven identification module 220 also formulates the smoothing term in equation 1:

$$\beta \sum_{K=1}^{c} f_k^T \Delta f_k.$$

This term enforces the neighborhood assumption of semi0supervised learning, i.e., if two patients are highly similar in the graph then they are likely to belong to the same risk group. Larger β will bias F more towards the graph structure as encoded by Δ.

The matching module 222 is configured to match the risk groups identified by data-driven insights and knowledge-driven insights in terms of pairwise relations. The matching module 222 formulates the matching term in equation 1:

$$-\mu \sum_{k=1}^{c} \sum_{l=1}^{c'} g_l^T (f_k f_k^T) g_l.$$

This term maximizes (note the negative sign before μ) the agreement between assignment F and assignment G in terms of pairwise relations. The value of $$\sum_{k=1}^{c} \sum_{l=1}^{c'} g_l^T (f_k f_k^T) g_l$$

is the total number of patient pairs whose relation F and G agree on. μ decides how close G and F must be to each other.

The solving module 224 is configured to solve the objective function of equation 1 to identify a set of risk groups in alignment with the input domain knowledge 216 and/or to identify additional risk groups not associated with the input domain knowledge 216. This results in identified risk groups 228 as an output 226.

If F and G are treated as two groups of variables, a Block Coordinate Descent (BCD) type of approach may be adopted to solve equation 1. This approach is an iterative method such that at each iteration, either F or G is fixed and J is minimized with respect to the other. In this case, fixing G solving F leads to graph transduction, while fixing F solving G leads to normalized min0cut. Unfortunately, solving either step of the alternating minimization process is NP hard in their original form. It will be shown below how to relax the objective to allow an efficient solution.

To solve a relaxed version of equation 1, F and G are first relaxed from binary assignment to soft assignment. The relaxed objective becomes equation 2.

$$\operatorname*{argmin}_{f_k, g_l \in \mathbb{R}^n} \alpha \sum_{k=1}^{c} \|f_k - y_k\|_{\mathcal{L}}^2 + \quad (2)$$

$$\beta \sum_{k=1}^{c} f_k^T \Delta f_k + \gamma \sum_{l=1}^{c'} g_l^T \Delta g_l - \mu \sum_{k=1}^{c} \sum_{l=1}^{c'} g_l^T (f_k f_k^T) g_l$$

$$\text{s.t. } G^T G = I_{c'}, G \geq 0$$

$I_{c'}$ is a c'×c' identity matrix. The orthogonality constraint of G stops trivial solutions. Note that it is unnecessary to pose the same constraint on F because F is already constrained by the fitting term to approximate Y.

After relaxation, given a fixed G, F is solved for:

$$\operatorname*{argmin}_{f_k \in \mathbb{R}^n} \alpha \sum_{k=1}^{c} \|f_k - y_k\|_{\mathcal{L}}^2 + \beta \sum_{k=1}^{c} f_k^T \left(I_n - \left(s + \frac{\mu}{\beta} G G^T\right)\right) f_k. \quad (3)$$

The objective in equation 3 can be solved in closed form:

$$F = (1-\rho)\left(I_n - \rho\left(S + \frac{\mu}{\beta} G G^T\right)\right)^{-1} Y, \quad (4)$$

where ρ=α/(α+β) and $S = I_n - \Delta$.

Given a fixed F, G is solved for:

$$\underset{g_l \in \mathbb{R}^n}{\text{argmin}} \sum_{l=1}^{c'} g_l^T \Delta g_l - \frac{\mu}{\gamma} \sum_{k=1}^{c} \sum_{l=1}^{c'} g_l^T (f_k f_k^T) g_l, \quad (5)$$
$$\text{s.t. } G^T G = I_{c'}, G \geq 0$$

Equation 5 is equivalent to:

$$\underset{g_l \in \mathbb{R}^n}{\text{argmin}} \sum_{l=1}^{c'} g_l^T \left( S + \frac{\mu}{\gamma} FF^T \right) g_l \quad (6)$$
$$\text{s.t. } G^T G = I_{c'}, G \geq 0$$

Since $FF^T$ is a kernel, $$S + \frac{\mu}{\gamma} FF^T$$

remains a positive semi-definite kernel. Equation 6 is a standard graph min-cut objective with non-negativity constraint and it can be solved by the multiplicative update rule:

$$G \leftarrow G \circ \sqrt{\frac{\left(S + \frac{\mu}{\gamma} FF^T\right) G}{G\left(G^T \left(S + \frac{\mu}{\gamma} FF^T\right) G\right)}} \quad (7)$$

∘ is the Hadamard product. G can be initialized by the cluster assignment from performing spectral clustering on S.

The alternating minimization process is guaranteed to converge because the objective in equation (2) is lower-bounded. The process of solving equation 1 is summarized below in Pseudocode 1.

Pseudocode 1: risk group analysis
Input: Similarity graph W, input labels $Y \in \{0,1\}^{n \times c}$, parameters c', β, γ, μ=1, ρ;
Output: Group indicator matrix $G \in \mathbb{R}^{n \times c'}$;
Normalize the graph kernel: $S \leftarrow D^{-1/2} W D^{-1/2}$, where D is the degree matrix of W;
Compute the normalized Laplacian: $\Delta \leftarrow I_n - S$;
Perform c'-way spectral clustering on S and initialize $G \in \{0,1\}^{n \times c'}$ as the corresponding group assignment matrix;
repeat:

---

$G' \leftarrow G$;

$F \leftarrow (1-\rho)\left(I_n - \rho\left(S + \frac{\mu}{\beta} G' G'^T\right)\right)^{-1} Y$;

$H \leftarrow G'$
repeat
$\quad H' \leftarrow H$;

$H \leftarrow H' \circ \sqrt{\frac{\left(S + \frac{\mu}{\gamma} FF^T\right) H'}{H'\left(H'^T \left(S + \frac{\mu}{\gamma} FF^T\right) H'\right)}}$;

until $\|H - H'\| \prec \in$;
$G \leftarrow H$;
until $\|G - G'\| < \in$;
return G ;

---

Implementation of pseudocode 1 will now be discussed.

Setting β, γ, μ; Since the ratio μ/β and μ/γ is the only concern, without loss of generality μ can be fixed to 1. 1/γ>0 decides the influence of $FF^T$ on S in equation 6. Smaller γ will make G biased more towards F rather than S. To balance the influence of the two kernels (S and $FF^T$), notice that the most significant cut of S comes from its second largest singular vector (its largest singular vector is a constant vector) and the most significant cut of $FF^T$ comes from its largest singular vector. Let SVD(X, k) denote the function that returns the k-th largest singular value of X, γ can be set to:

$$\gamma = SVD(FF^T, 1)/SVD(S, 2) \quad (8)$$

This scales the influence of $FF^T$ to the same level of the normalized min-cut of S. Similarly, the ratio 1/β controls the influence of $FF^T$ on S in equation 4. Since the given labels in Y should be preserved in this implementation, β is set to a large number such that 1/β will be small (e.g., 0.1).

Setting ρ: $\rho \in (0,1)$ is a tradeoff factor between the graph structure and the input labels. Larger ρ will make F biased more towards the normalized min-cut of $$S + \frac{\mu}{\beta} GG^T.$$

In this implementation, a simple heuristic is used to set ρ:

$$\rho = \left(1 - \frac{|\mathcal{L}|}{n}\right) \alpha_1 + \alpha_2, \forall a_1, a_2 \geq 0, \alpha_1 + \alpha_2 < \frac{\beta}{\beta + \mu c'}. \quad (9)$$

Equation 9 bounds the value of ρ between $a_1$ and $a_2$, and the value of ρ will decrease when the number of labeled nodes increases (thus F must adhere more strictly to Y).

Setting c': Ideally, c'>c is the true number of risk groups in the patient cohort. c' is preferably set by domain experts. If sufficient domain knowledge is lacking, c' could be set in two different ways. One way is to set c'=c+1, which essentially merges all risk groups into one meta-group. The other is to estimate c' through a regularizer.

Complexity: Inside each iteration, the complexity of the present approach is dominated by that of Learning with Local and Global Consistency (LLGC, equation 4) and non-negative min-cut (equation 6). The complexity of LLGC is dominated by computing the pseudoinverse of an n×n matrix, which is $O(n^3)$ in the worst case. The complexity of non-negative normalized min-cut is $O(n^2 k)$, where k is the number of iterations needed to converge. An extra $O(n^2 c')$ time is needed to initialize G using c'-way spectral clustering.

Figure 5:
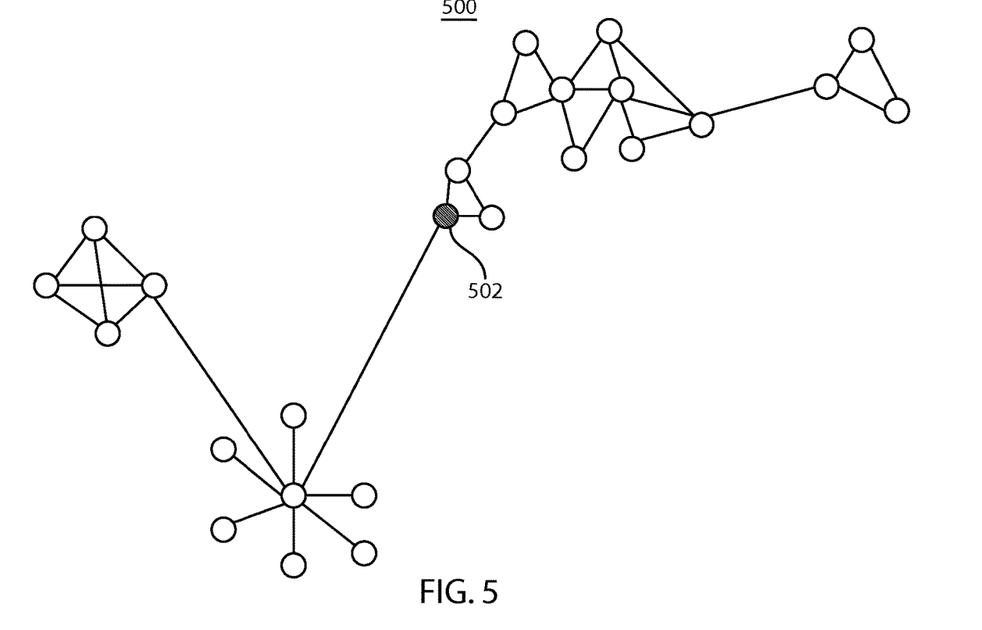
FIG. 5 shows an exemplary patient similarity network graph having knowledge-driven insights injected therein in accordance with one illustrative embodiment.

Referring now to FIG. 5, an exemplary patient similarity network graph 500 is illustratively depicted in accordance with one embodiment. The patient similarity graph 500 shows the injection of knowledge-driven insights. Knowledge-driven insights are data from domain experts (e.g., physicians). The present invention allows the introduction of knowledge-driven insights to the patient similarity network graph 500 in the form of known risk factors or other data from domain experts. For example, domain experts may determine that patient node 502 may be associated with severe chronic kidney disease risk factor, which may be used to identify the risk group associated with that risk factor. The present invention enforces the knowledge by trying to align the identified risk groups with given risk factors.

Figure 6:
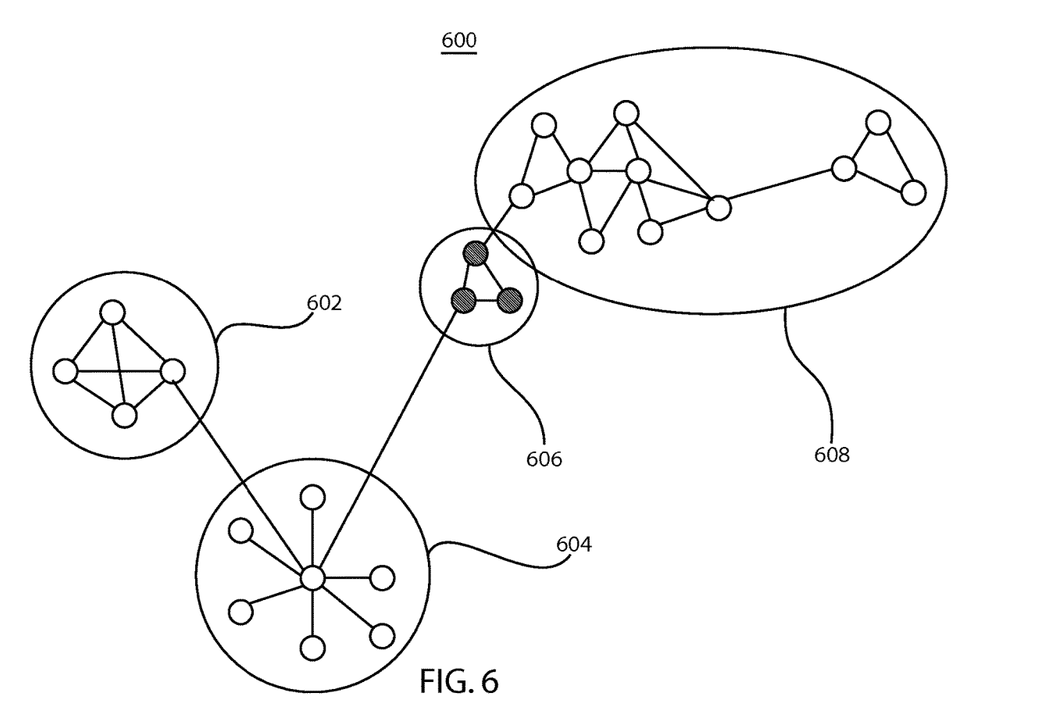
FIG. 6 shows an exemplary patient similarity network graph having risk groups from both data-driven insights and knowledge-driven insights in accordance with one illustrative embodiment.

Referring now to FIG. 6, an exemplary patient similarity network graph 600 is illustratively depicted in accordance with one embodiment. The patient similarity network graph 600 includes risk groups 602, 604, 606, 608 identified using both data-driven and knowledge-driven insights. For example, risk group 602 may be labeled "skin disease" having risk factors such as dermatoses, malignant neoplasm of skin, etc., risk group 604 may be labeled "heart disease" having risk factors such as heart arrhythmias, chronic ischemic heart disease, etc., risk group 606 be labeled "kidney disease" having risk factors such as chronic renal failure, acute renal failure, etc., and risk group 608 may be labeled "eye disease" having risk factors such as glaucoma, cataract, etc. Risk groups identified with both data-driven and knowledge-driven insights are more interpretable because they align with domain knowledge and the ambiguity from the underlying network is resolved. The identified risk groups may be used to extract additional risk factors and risk scores, which may be used, e.g., in a personalized health care delivery system.

The present invention incorporates both knowledge-driven insights and data-driven insights. Advantageously, the present invention is graph-based and, therefore, can identify risk groups form a patient similarity network without access to the raw clinical features. The present invention can also incorporate incomplete and very sparse domain knowledge.

Figure 7:
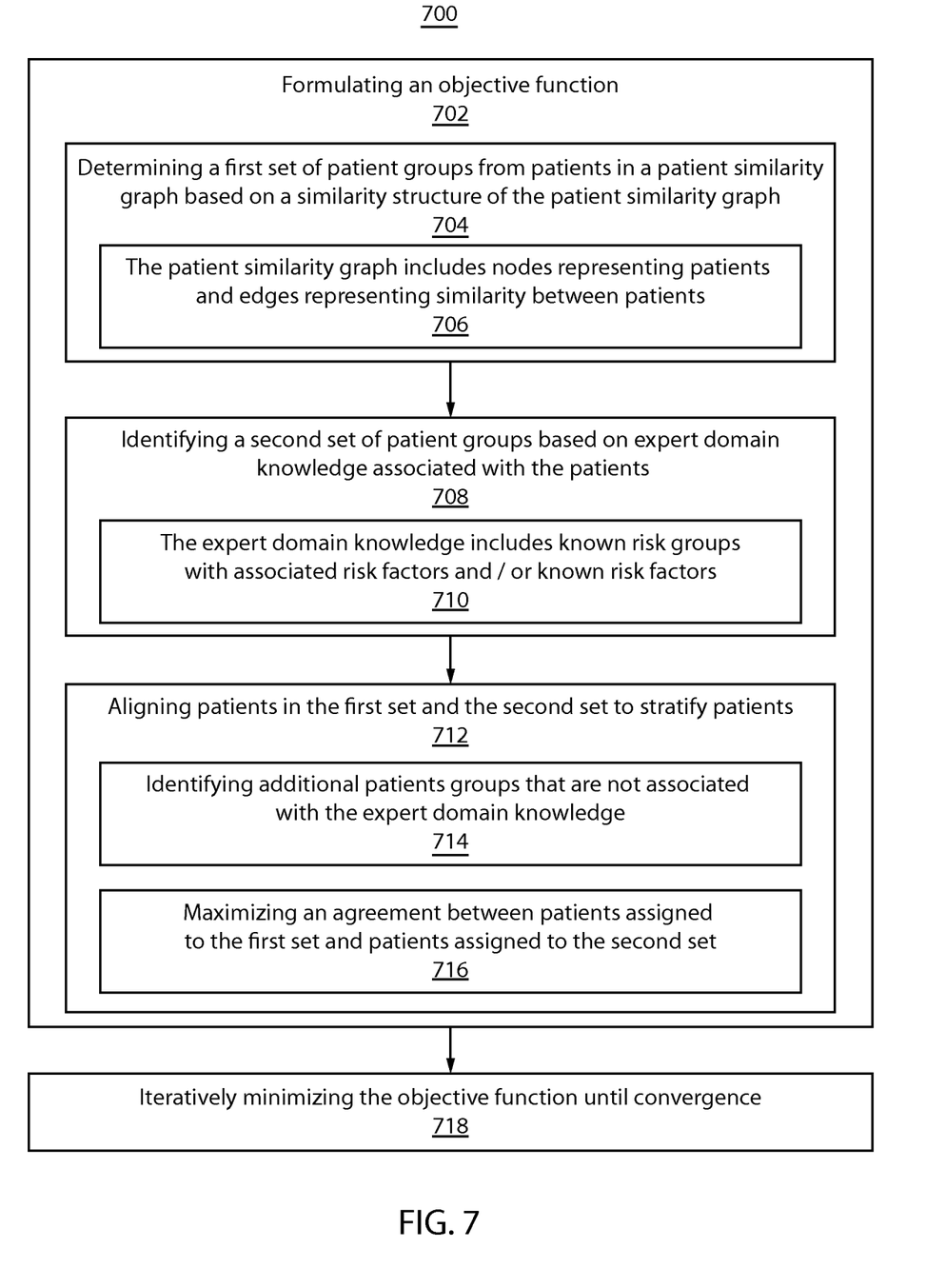
FIG. 7 is a block/flow diagram showing a method for patient risk stratification in accordance with one illustrative embodiment.

Referring now to FIG. 7, a block/flow diagram showing a method for patient stratification 700 is illustratively depicted in accordance with one embodiment. In block 702, an objective function is formulated. In block 704, the objective function may determine a first set of patient groups from patients in a patient similarity graph based on a similarity structure of the patient similarity graph. The patient similarity graph may be formed from patient data, e.g., EMR database. In block 706, the patient similarity graph includes nodes representing patients and edges representing similarity between patients. The patient similarity graph has limited access to raw features of the patients.

In block 708, the objective function may identify a second set of patient groups based on expert domain knowledge associated with the patients. The second set of patient groups preferably includes incomplete information (e.g., unseen classes). In block 710, the expert domain knowledge includes known risk groups with associated risk factors and/or known risk factors. In block 712, the objective function may include aligning patients in the first set and the second set to stratify patients. In block 714, aligning patients may include identifying additional patient groups that are not associated with the expert domain knowledge. In block 716, aligning patients may include maximizing an agreement between patients assigned to the first set and patients assigned to the second set.

In block 718, the objective function is iteratively minimized until convergence. This may include applying Block Coordinate Descent.

Having described preferred embodiments of a system and method for patient risk stratification by combining knowledge-driven and data-driven insights (which are intended to be illustrative and not limiting), it is noted that modifications and variations can be made by persons skilled in the art in light of the above teachings. It is therefore to be understood that changes may be made in the particular embodiments disclosed which are within the scope of the invention as outlined by the appended claims. Having thus described aspects of the invention, with the details and particularity required by the patent laws, what is claimed and desired protected by Letters Patent is set forth in the appended claims.

What is claimed is:

1. A computer-implemented method comprising:
building, by at least one processor device operatively coupled to memory, an electronic medical records (EMR) database storing medical event data and a domain experts database storing expert domain knowledge data provided by domain experts;
obtaining, by the at least one processor device using the EMR database and the domain experts database, a customized treatment plan based on a prediction model using customized risk factors by:
determining a first set of patient groups from patients in a patient similarity graph using a similarity structure of the patient similarity graph, the patient similarity graph being generated based on the EMR database and comprising nodes that represent patients and edges that each represent a similar medical condition for connected nodes;
identifying a second set of patient groups using the domain experts database; and
aligning patients in the first set and the second set using a processor to stratify patients, the alignment of patients including minimizing an objective function based on a soft assignment of patients into the first set of patient groups and the second set of patient groups, to output a set of risk groups, each of which includes patients having consistent clinical conditions, wherein soft assignment comprises assigning a non-binary value for each patient's membership in each group; and
triggering, by the at least one processor device, delivery of personalized healthcare to the stratified patients using the customized treatment plan.

2. The method as recited in claim 1, wherein aligning patients includes identifying additional patient groups that are not associated with the expert domain knowledge.

3. The method as recited in claim 1, wherein aligning patients includes maximizing an agreement between patients assigned to the first set and patients assigned to the second set.

4. The method as recited in claim 1, wherein the expert domain knowledge includes known risk factors associated with the patients.

5. The method as recited in claim 1, wherein the second set of patient groups is incomplete.

6. The method as recited in claim 5, wherein the second set of patient groups includes unseen classes.

7. The method as recited in claim 1, wherein aligning further comprises iteratively minimizing the objective function until convergence.

8. The method as recited in claim 1, wherein the patient groups include patient risk groups for a medical condition.

9. A non-transitory computer readable storage medium comprising a computer readable program, wherein the computer readable program when executed by a computer causes the computer to perform the steps of: building an electronic medical records (EMR) database storing medical event data and a domain experts database storing expert domain knowledge data provided by domain experts;
obtaining, using the EMR database and the domain experts database, a customized treatment plan based on a prediction model using customized risk factors by:
determining a first set of patient groups from patients in a patient similarity graph using a similarity structure of the patient similarity graph, the patient similarity graph being generated based on the EMR database and comprising nodes that represent patients and edges that each represent a similar medical condition for connected nodes;

identifying a second set of patient groups using the domain experts database; and aligning patients in the first set and the second set using a processor to stratify patients, the alignment of patients including minimizing an objective function based on a soft assignment of patients into the first set of patient groups and the second set of patient groups, to output a set of risk groups, each of which includes patients having consistent clinical conditions, wherein soft assignment comprises assigning a non-binary value for each patient's membership in each group; and triggering delivery of personalized healthcare to the stratified patients using the customized treatment plan.

10. The computer readable storage medium as recited in claim 9, wherein aligning patients includes identifying additional patient groups that are not associated with the expert domain knowledge.

11. A system comprising:

at least one processor device operatively coupled to memory configured to:

build an electronic medical records (EMR) database storing medical event data and a domain experts database storing expert domain knowledge data provided by domain experts;

obtain, using the EMR database and the domain experts database, a customized treatment plan based on a prediction model using customized risk factors by:

determining a first set of patient groups from patients in a patient similarity graph using a similarity structure of the patient similarity graph, the patient similarity graph being generated based on the EMR database and comprising nodes that represent patients and edges that each represent a similar medical condition for connected nodes;

identifying a second set of patient groups using the domain experts database; and stratifying patients by minimizing an objective function based on a soft assignment of patients into the first set of patient groups and the second set of patient groups, to output a set of risk groups, each of which includes patients having consistent clinical conditions, wherein soft assignment comprises assigning a non-binary value for each patient's membership in each group; and trigger a personalized healthcare delivery system to deliver personalized healthcare to the stratified patients using the customized treatment plan.

12. The system as recited in claim 11, wherein the matching module is further configured to identify additional patient groups that are not associated with the expert domain knowledge.

13. The system as recited in claim 11, wherein the matching module is further configured to maximize an agreement between patients assigned to the first set and patients assigned to the second set.

14. The system as recited in claim 11, wherein the expert domain knowledge includes known risk factors associated with the patients.

15. The system as recited in claim 11, wherein the first set of patient groups is incomplete.

16. The system as recited in claim 15, wherein the first set of patient groups includes unseen classes.

17. The system as recited in claim 11, wherein the at least one processor device is further configured to iteratively minimize the objective function until convergence.

18. The system as recited in claim 11, wherein the patient groups include patient risk groups for a medical condition.

19. The method as recited in claim 1, wherein the objective function comprises a group term that represents a data-driven exploration of the patient similarity graph, a fitting term that governs how well soft assignments of patients to the first set of patient groups needs to fit the expert domain knowledge, a smoothing term that enforces a neighborhood assumption of supervised learning, and a matching term that maximizes the agreement between the soft assignment of patients to the first set of patient groups and a soft assignment of patients to the second set of patient groups.

20. The method as recited in claim 1, wherein triggering delivery of the personalized healthcare to the stratified patients using the customized treatment plan further includes administering treatment to the stratified patients.

* * * * *